United States Patent
Meeks et al.

(10) Patent No.: US 10,338,009 B2
(45) Date of Patent: Jul. 2, 2019

(54) METHOD AND APPARATUS TO DETECT DEFECTS IN TRANSPARENT SOLIDS

(71) Applicant: Zeta Instruments, Inc., San Jose, CA (US)

(72) Inventors: Steven W. Meeks, Palo Alto, CA (US); Ronny Soetarman, Fremont, CA (US)

(73) Assignee: KLA-TENCOR CORPORATION, Milpitas, CA (US)

( * ) Notice: Subject to any disclaimer, the term of this patent is extended or adjusted under 35 U.S.C. 154(b) by 0 days.

(21) Appl. No.: 15/607,648

(22) Filed: May 29, 2017

(65) Prior Publication Data

US 2017/0261440 A1    Sep. 14, 2017

Related U.S. Application Data

(63) Continuation of application No. 14/449,058, filed on Jul. 31, 2014, now Pat. No. 9,784,691.

(51) Int. Cl.
*G01N 21/958* (2006.01)
*G01N 21/47* (2006.01)

(52) U.S. Cl.
CPC ........... *G01N 21/958* (2013.01); *G01N 21/47* (2013.01); *G01N 2021/4711* (2013.01); *G01N 2021/4735* (2013.01)

(58) Field of Classification Search
CPC .............. G01N 21/4738; G01N 21/47; G01N 2021/4704; G01N 2021/4709; G01N 2021/4711; G01N 2021/4714; G01N 2021/4721; G01N 2021/4723
See application file for complete search history.

(56) References Cited

U.S. PATENT DOCUMENTS

| | | | | | |
|---|---|---|---|---|---|
| 5,864,394 | A | * | 1/1999 | Jordan, III | G01N 21/94 257/E21.53 |
| 2004/0051862 | A1 | * | 3/2004 | Alcock | G01N 21/474 356/71 |
| 2005/0094136 | A1 | * | 5/2005 | Xu | G01N 21/21 356/237.3 |
| 2008/0075353 | A1 | * | 3/2008 | Tek | G01N 21/4738 382/145 |
| 2010/0007872 | A1 | * | 1/2010 | Isozaki | G01N 21/47 356/51 |

(Continued)

*Primary Examiner* — Michael P LaPage
(74) *Attorney, Agent, or Firm* — Imperium Patent Works LLP; Mark D. Marrello

(57) ABSTRACT

A method and apparatus to measure specular reflection intensity, specular reflection angle, near specular scattered radiation, and large angle scattered radiation and determine the location and type of defect present in a first and a second transparent solid that have abutting surfaces. The types of defects include a top surface particle, an interface particle, a bottom surface particle, an interface bubble, a top surface pit, and a stain. The four measurements are conducted at multiple locations along the surface of the transparent solid and the measured information is stored in a memory device. The difference between an event peak and a local average of measurements for each type of measurement is used to detect changes in the measurements. Information stored in the memory device is processed to generate a work piece defect mapping indicating the type of defect and the defect location of each defect found.

20 Claims, 18 Drawing Sheets

(56) References Cited

U.S. PATENT DOCUMENTS

| | | | | |
|---|---|---|---|---|
| 2012/0081701 | A1* | 4/2012 | Sasazawa | G01N 21/8851 |
| | | | | 356/237.2 |
| 2013/0258320 | A1* | 10/2013 | Funaki | G01N 21/95 |
| | | | | 356/73 |
| 2015/0116702 | A1* | 4/2015 | Matsumoto | G01N 21/9501 |
| | | | | 356/237.5 |

* cited by examiner

TRANSPARENCY MAY BE IN THE VISIBLE SPECTRUM OR THE INFRARED SPECTRUM.
GLASS IS TRANSPARENT IN THE VISIBLE AND SILICON IS TRANSPARENT IN THE INFRARED.

**TRANSPARENT LAYERS INTERFACE
(CROSS-SECTIONAL VIEW)**

TRANSPARENT LAYERS INTERFACE
(CROSS-SECTIONAL VIEW)

SPECULAR REFLECTION MAPPING

SPECULAR REFLECTION DUE TO AIR GAP
(CROSS-SECTIONAL VIEW)

SPECULAR REFLECTION MAPPING

**TOP SURFACE PARTICLE FORWARD SCATTERED RADIATION
(CROSS-SECTIONAL VIEW)**

**TOP SURFACE PARTICLE BACK SCATTERED RADIATION
(CROSS-SECTIONAL VIEW)**

LARGE ANGLE SCATTERED RADIATION MAPPING

BOTTOM SURFACE PARTICLE BACK SCATTERED RADIATION
(CROSS-SECTIONAL VIEW)

PRESENCE OF A SINGLE EVENT IN THE LARGE ANGLE SCATTERED RADIATION MAP
INDICATES THAT A BOTTOM PARTICLE IS PRESENT AT THE SCANNING LOCATION.

LARGE ANGLE SCATTERED RADIATION MAPPING

SCATTERED RADIATION IS PREDOMINATELY IN THE UPWARD DIRECTION ALONG THE PATH OF NSSR. (SIMILAR TO A TOP SURFACE PIT, EXCEPT THERE IS NO CHANGE IN THE SPECULAR REFLECTIVITY WHEN A SMALL PARTICLE PRESENT.

**NEAR SPECULAR SCATTERED RADIATION DUE TO A SMALL INTERFACE PARTICLE
(CROSS-SECTIONAL VIEW)**

NEAR SPECULAR SCATTERED RADIATION MAPPING

NEAR SPECULAR SCATTERED RADIATION DUE TO TOP SURFACE PIT
(CROSS-SECTIONAL VIEW)

NEAR SPECULAR SCATTERED RADIATION MAPPING

FIG. 15 OPTICAL INSPECTOR — TOP VIEW

OPTICAL INSPECTOR
TOP VIEW

LARGE ANGLE SCATTERED RADIATION OPTICAL INSPECTOR

SPECULAR REFLECTION INTENSITY MAPPING

SCATTERED RADIATION INTENSITY MAPPING

| LARGE ANGLE SCATTERED RADIATION | NEAR SPECULAR SCATTERED RADIATION | SPECULAR REFLECTION INTENSITY | SPECULAR REFLECTION ANGLE (SURFACE SLOPE) | DEFECT TYPE |
|---|---|---|---|---|
| NONE OR MUCH LESS THAN NSSR | MUCH GREATER THAN LASR | NONE OR POSITIVE | POSITIVE SLOPE FOLLOWED BY NEGATIVE SLOPE, OR CONSTANT. | INTERFACE PARTICLE (MINIMAL AIR GAP) |
| NONE OR MUCH LESS THAN NSSR | MUCH GREATER THAN LASR | LARGE POSITIVE | OSCILLATING SLOPES | INTERFACE BUBBLE (SIGNIFICANT AIR GAP) |
| "DOUBLE EVENT" MUCH GREATER THAN NSSR | LESS THAN LASR | NONE OR NEGATIVE | CONSTANT SLOPE | TOP SURFACE PARTICLE |
| "SINGLE EVENT", GREATER THAN NSSR | LESS THAN LASR | NONE | CONSTANT SLOPE | BOTTOM SURFACE PARTICLE |
| NONE OR LESS THAN NSSR | MUCH GREATER THAN LASR | NEGATIVE | NEGATIVE SLOPE FOLLOWED BY POSITIVE SLOPE, OR CONSTANT SLOPE | TOP SURFACE PIT |
| POSITIVE | LESS THAN LASR | NEGATIVE | CONSTANT SLOPE | STAIN |

LASR = LARGE ANGLE SCATTERED RADIATION = DIFFERENCE BETWEEN EVENT PEAK AND LOCAL AVERAGE OF LARGE ANGLE SCATTERED RADIATION.

NSSR = NEAR SPECULAR SCATTERED RADIATION = DIFFERENCE BETWEEN EVENT PEAK AND LOCAL AVERAGE OF NEAR SPECULAR SCATTERED RADIATION.

SR = SPECULAR REFLECTION INTENSITY = DIFFERENCE BETWEEN EVENT PEAK AND LOCAL AVERAGE OF SPECULAR REFLECTION.

SPECULAR REFLECTION ANGLE = DIFFERENCE BETWEEN EVENT PEAK AND LOCAL AVERAGE OF SPECULAR REFLECTION ANGLE (SURFACE SLOPE).

DEFECT DETECTION AND CLASSIFICATION LOGIC TABLE

FIG. 20

DEFINITION OF EVENT INTENSITIES

WORK PIECE DEFECT MAPPING

DEFECT DETECTION FLOWCHART

SEPARATION MIRROR POSITION

METHOD AND APPARATUS TO DETECT DEFECTS IN TRANSPARENT SOLIDS

CROSS REFERENCE TO RELATED APPLICATION

This application is a continuation of, and claims priority under 35 U.S.C. § 120 from, nonprovisional U.S. patent application Ser. No. 14/449,058 entitled "A METHOD AND APPARATUS TO DETECT DEFECTS IN TRANSPARENT SOLIDS," filed on Jul. 31, 2014, and published as U.S. Pat. Pub. No. 2016/0033421. The disclosure of the foregoing document is incorporated herein by reference.

TECHNICAL FIELD

The described embodiments relate generally to detecting defects and more particularly to detecting defects in a two transparent solids with abutting surfaces.

BACKGROUND INFORMATION

Transparent solids are used to form various products such as display and touch screen devices. The inspection of transparent solids is complicated by the difficulty of separating the scattered light reflected from the top and bottom surfaces of a transparent solid. This difficulty is further complicated when a first transparent solid is located on a second transparent solid.

SUMMARY

A surface optical inspector directs a source beam onto a surface of a transparent solid that is placed on top of a second and in response measures various types of radiation from the work piece. The types of radiation include specular reflection, specular reflection angle, near specular scattered radiation, and large angle scattered radiation. The measured information is processed to determine the total reflectivity of the work piece, the surface slope of the work piece, large angle scattered radiation intensity from the work piece, and near specular scattered radiation intensity from the work piece. These measurements are in turn utilized to determine the type of defect present at the scan location and on which surface of which transparent solid the defect is located.

In a first novel aspect, a scanning beam is directed to a first location on a first surface of a first transparent solid and a second surface of the first transparent solid abuts a first surface of a second transparent solid. At the first location the following measurements are made: (i) specular reflection intensity, (ii) Near Specular Scattered Radiation (NSSR) intensity, (iii) Large Angle Scattered Radiation (LASR) intensity, and (iv) Specular Reflection Angle. Measurements (i) through (iv) result from irradiation by the scanning beam. Then coordinate values of the first location, and measurements (i) through (iv) are stored in a memory.

In one example, the measurements are measured across the entire surface of the first transparent solid. At each location along the surface of the transparent solid a determination as to what type of defect is present at the location. The types of defects are selected from a group comprising: (1) a top surface particle, (2) an interface particle, (3) a bottom surface particle, (4) an interface bubble, (5) a top surface pit, and (6) a stain.

In a second novel aspect, a type of defect at the first location is an interface particle when: (i) the LASR measured at the first location less than a first percentage (fifty-percent) of the NS SR measured at the first location; (ii) the specular reflection intensity measured at the first location is within a second percentage (a tenth of a percent) of a local average of specular reflection intensity or greater; and (iii) the specular reflection angle transitions from a positive angle to a negative angle at the first location. The local averages are a function of multiple measurements measured at a multiple locations that are within a first distance of the first location.

In a third novel aspect, the type of defect at the first location is an interface bubble when: (i) the LASR measured at the first location is less than a first percentage (fifty percent) of the NSSR measured at the first location; (ii) the specular reflection intensity measured at the first location is more than a second percentage (one half of one percent) greater than a local average of specular reflection intensity or greater; and (iii) the specular reflection angle oscillates between positive angles and negative angles near the first location. The local averages are a function of multiple measurements measured at a multiple locations that are within a first distance of the first location.

In a fourth novel aspect, type of defect at the first location is a top surface particle when: (i) the LASR measured at the first location is more than a first percentage (twice as large) of the LASR measured at the second location, and the LASR measured at a first location is more than a second percentage (twice as large) of the NSSR measured at the first location, wherein the first location is within a first distance of the second location; (iii) the specular reflection intensity measured at the first location is within a third percentage (ten percent) of a local average of specular reflection intensity, or more; (iv) the specular reflection angle is within a fourth percentage (one percent) of a local average of specular reflection angles. The local averages are a function of multiple measurements measured at a multiple locations that are within a first distance of the first location.

In a fifth novel aspect, the type of defect at the first location is bottom surface particle when: (i) the LASR measured at the first location is at least a first percentage (twice as large) of the NSSR measured at the first location; (ii) the specular reflection intensity measured at the first location is within a second percentage (one percent) of the local average of specular reflection intensity; and (iii) the specular reflection angle is within a third percentage (one percent) of a local average of specular reflection angles. The local averages are a function of multiple measurements measured at a multiple locations that are within a first distance of the first location.

In a sixth novel aspect, the type of defect at the first location is top surface pit when: (i) the LASR measured at the first location is within a first percentage (one percent) of a local average of LASR, and less than a second percentage (fifty percent) of the NSSR measured at the first location; (ii) the specular reflection intensity measured at the first location is at least a third percentage (tenth of a percent) less than a local average of specular reflection intensity; and (iii) the specular reflection angle transitions from a negative angle to a positive angle at the first location. The local averages are a function of multiple measurements measured at a multiple locations that are within a first distance of the first location.

In a seventh novel aspect, type of defect at the first location is a stain when: (i) the LASR measured at the first location is at least a first percentage (tenth of a percent) greater than a local average of LASR intensities; (ii) the NSSR measured at the first location is less than the LASR intensity measured at the first location; (iii) the specular reflection intensity measured at the first location is less than a local average of specular reflection intensities; and (iv) the specular reflection angle is within a second percentage (one percent) of a local average of specular reflection angles. The local averages are a function of multiple measurements measured at a multiple locations that are within a first distance of the first location.

Further details and embodiments and techniques are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 20 is a diagram of defect detection and classification logic table.

DETAILED DESCRIPTION

Reference will now be made in detail to background examples and some embodiments of the invention, examples of which are illustrated in the accompanying drawings. In the description and claims below, relational terms such as "top", "down", "upper", "lower", "top", "bottom", "left" and "right" may be used to describe relative orientations between different parts of a structure being described, and it is to be understood that the overall structure being described can actually be oriented in any way in three-dimensional space.

Figure 1:
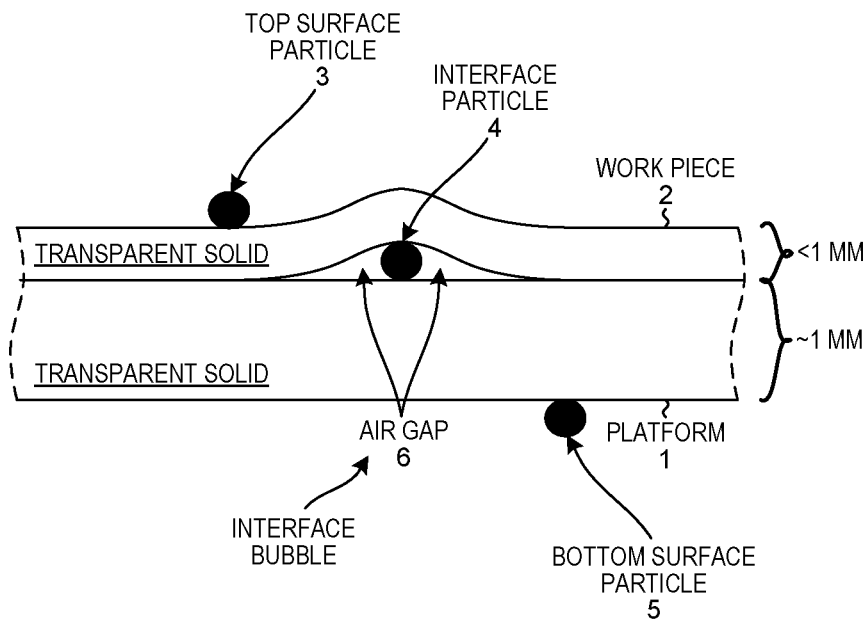
FIG. 1 is a cross-sectional diagram illustrating the interface of two transparent solids.

FIG. 1 is a cross-sectional diagram illustrating the interface of two transparent solids. During the fabrication of transparent solids (also referred to transparent work pieces, transparent layers, transparent wafers, and transparent discs) unwanted defects can be produced. These unwanted defects include a top surface particle 3, an interface particle 4, a bottom surface particle 5, an air gap, (also referred to as a "bubble") 6, and a top surface pit 22 illustrated in FIG. 13. These defects may occur in various locations on the transparent solids. These defects result in undesirable results such as reduced operating life of the resulting display device, non-functionality of the resulting display device, and degraded performance (light efficiency) of the resulting display device. It is valuable to a display manufacturer to detect these defects before additional resources are spent developing a product that will not function properly due to wafer level defects. For example, a "bubble" at the interface may produce unwanted topography on the top surface of the transparent solid and this may interfere with the ability to focus a lithography pattern on the surface. Particles on the top surface may cause electrical shorts to appear when metal lines are deposited on this surface.

It is noted herein, the example of two layers of glass is used for exemplary use only. This disclosure is not limited to the detection of defects in two layers of glass. Rather, this disclosure is applicable to all transparent layers or wafers or discs regardless of the specific material constituting the layer/wafer/disc or the end device to be manufactured with the developed layers/wafer/disc. For example, silicon is opaque in the visible range of the spectrum but transparent in the infrared spectrum. As a result this disclosure applies to the case of a work piece consisting of glass and a platform composed of silicon when the illuminating wavelength is in the infrared spectrum. It would also encompass the reverse case of a work piece consisting of silicon and a platform consisting of glass.

The first transparent solid 2 in FIG. 1 is a less than one millimeter thick. The second transparent solid 1 in FIG. 1 is approximately one millimeter thick. The second transparent solid 1 acts as a platform to hold the thinner and less durable first transparent solid which is referred to as a work piece.

Figure 2:
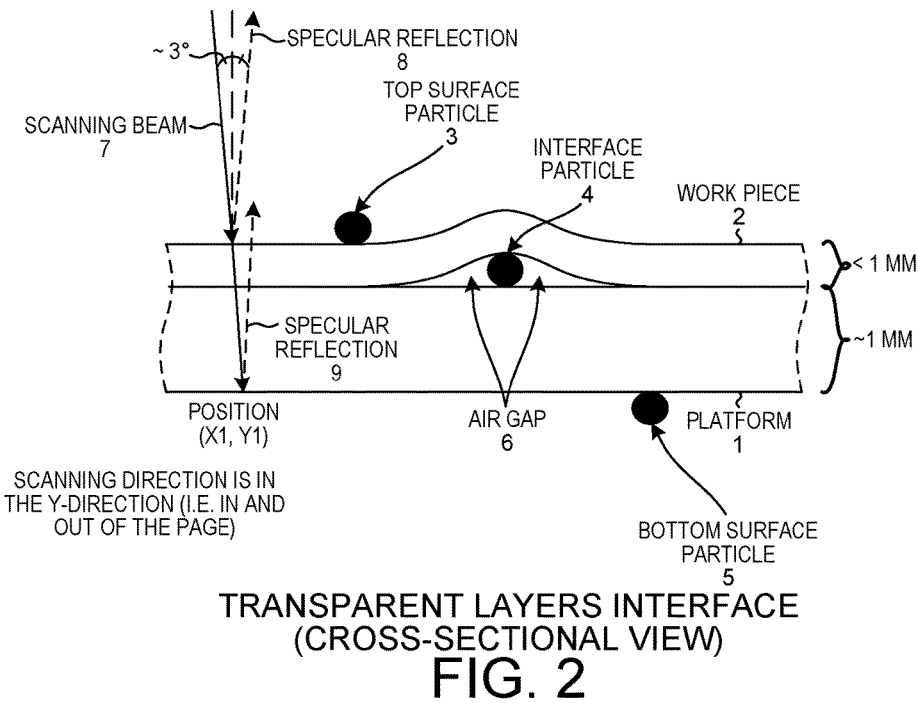
FIG. 2 is a cross-sectional diagram illustrating the interface of two transparent solids with a scanning beam directed at position located at (X1, Y1).

FIG. 2 is a cross-sectional diagram illustrating the interface of two transparent solids with a scanning beam 7 directed at position located at (X1, Y1). The scanning beam 7 scans across the work piece 2 in a direction going in the Y-direction (in and out of the page). Significant specular reflection 8 is reflected from the top surface of the work piece 2. Significant specular reflection 9 is also reflected from the bottom surface of the carrier 1. Specular reflections 8 and 9 are of similar intensity. There is no significant specular reflection from the interface between the work piece 2 and the platform 1 at position (X1, Y1) because the work piece 2 and the platform 1 are in intimate contact at position (X1, Y1) and because the work piece 2 and the platform 1 have a similar index of refraction.

Figure 3:
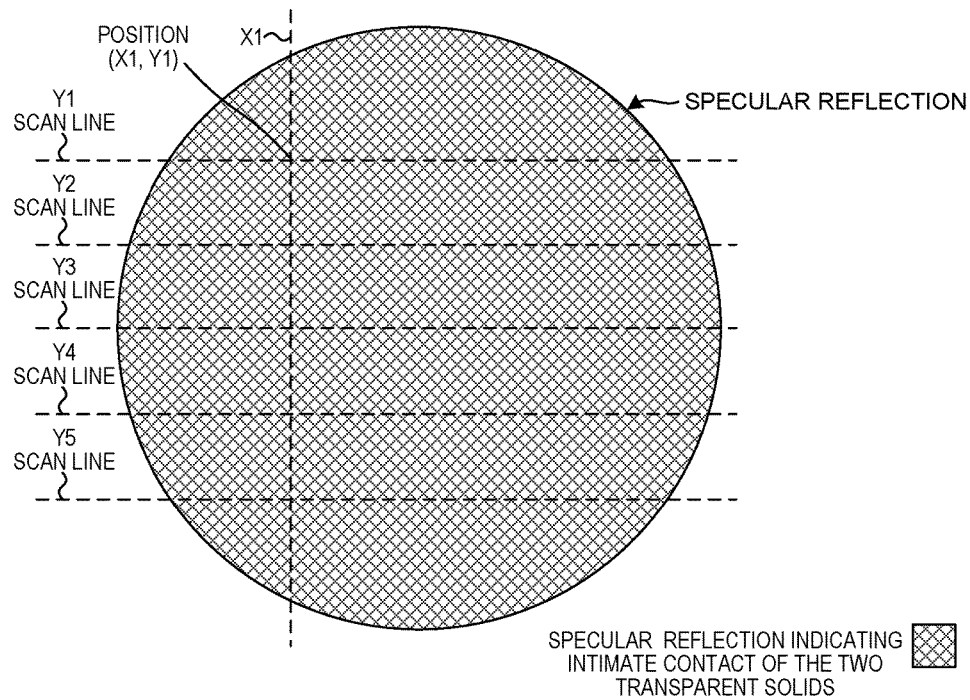
FIG. 3 is a specular reflection mapping illustrating the specular reflection resulting from the irradiation at position (X1, Y1).

FIG. 3 is a specular reflection mapping illustrating the specular reflection resulting from the irradiation at position (X1, Y1) illustrated in FIG. 2. The specular reflection intensity at position (X1, Y1) indicates that that the work piece 2 and the platform 1 are in intimate contact and that no particles or pits are present at location (X1, Y1).

Figure 4:
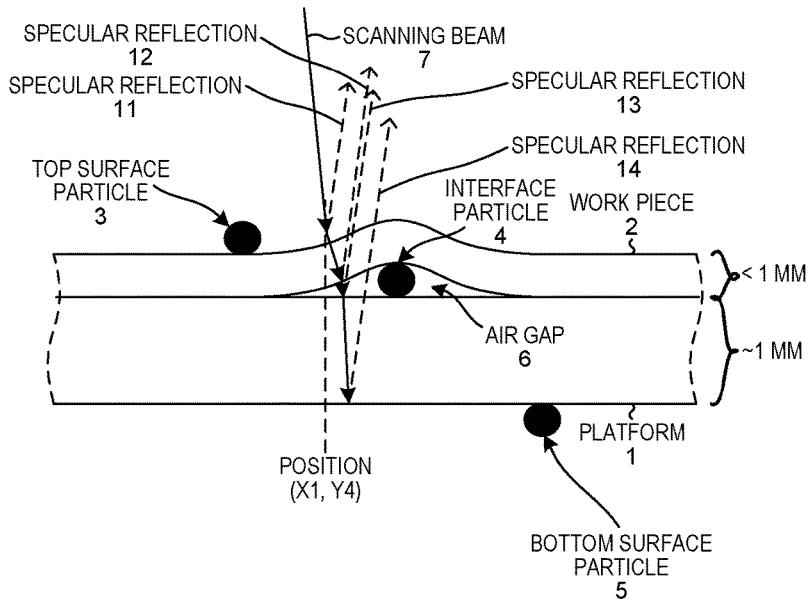
FIG. 4 is a cross-sectional diagram illustrating the interface of two transparent solids with a scanning beam directed at position located at (X1, Y4).

FIG. 4 is a cross-sectional diagram illustrating the interface of two transparent solids, work piece 2 and platform 1, with a scanning beam 7 directed at position located at (X1, Y4). Significant specular reflection 11 is reflected from the top surface of the work piece 2 due to the change of the index of refraction of air and the index of refraction of work piece 2. Significant specular reflection 12 is reflected from the bottom surface of the work piece 2 due to the change in the index of refection of the work piece 2 and index of refraction of the air trapped in air gap 6. Significant specular reflection 13 is reflected from the top surface of platform 1 due to the change in the index of refraction of the air trapped in air gap 6 and the index of refraction of platform 1. Significant specular reflection 14 is reflected from the bottom surface of platform 1 due to the change in the index of refraction of the platform to the index of refraction of air.

Figure 5:
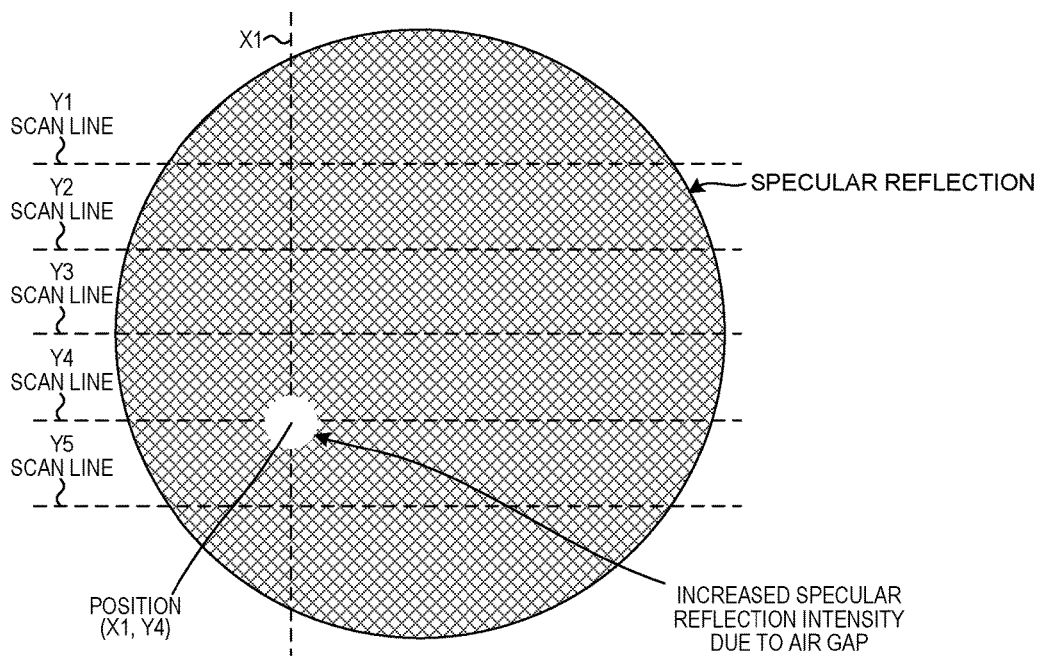
FIG. 5 is a specular reflection mapping illustrating the specular reflection resulting from the irradiation at position (X1, Y4).

FIG. 5 is a specular reflection mapping illustrating the specular reflection resulting from the irradiation at position (X1, Y4). As illustrated in FIG. 4, specular reflections 11-14 do not directly overlap, but rather are spread across a wide area. Accordingly, increased specular reflection intensity is observed at (X1, Y4) in the resulting specular reflection mapping shown in FIG. 5 indicating the presence of an air gap at location (X1, Y4).

Figure 6:
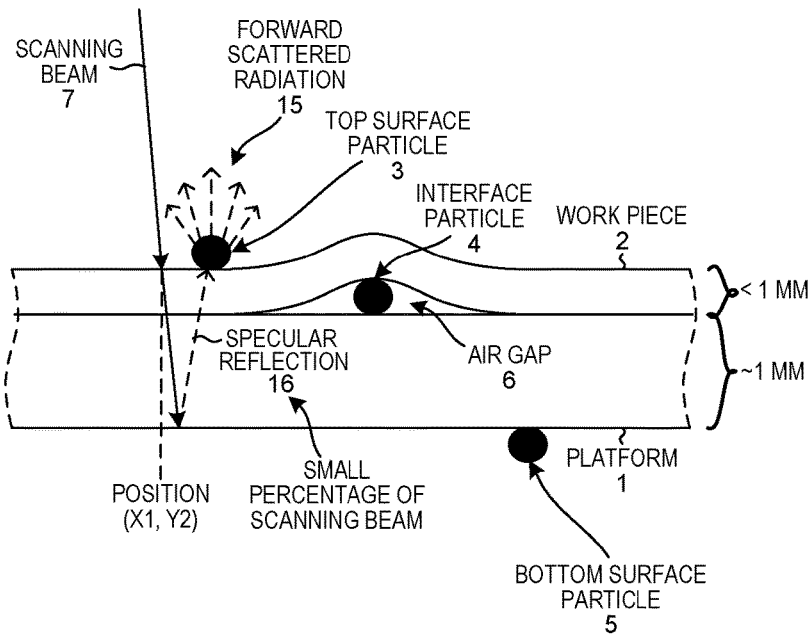
FIG. 6 is a cross-sectional diagram illustrating the interface of two transparent solids with a scanning beam directed at position located at (X1, Y2) causing top surface forward scattered radiation caused by a top surface particle.

FIG. 6 is a cross-sectional diagram illustrating the interface of two transparent solids with a scanning beam directed at position located at (X1, Y2) causing top surface forward scattered radiation caused by a top surface particle 3. Significant forward scattered radiation 15 is radiates from top surface particle 3 due to irradiation of the top surface particle 3 by specular reflection 16 which reflects from the bottom surface of platform 1. Specular reflection 16 is caused by the change of the index of refraction between the platform 1 and air.

Figure 7:
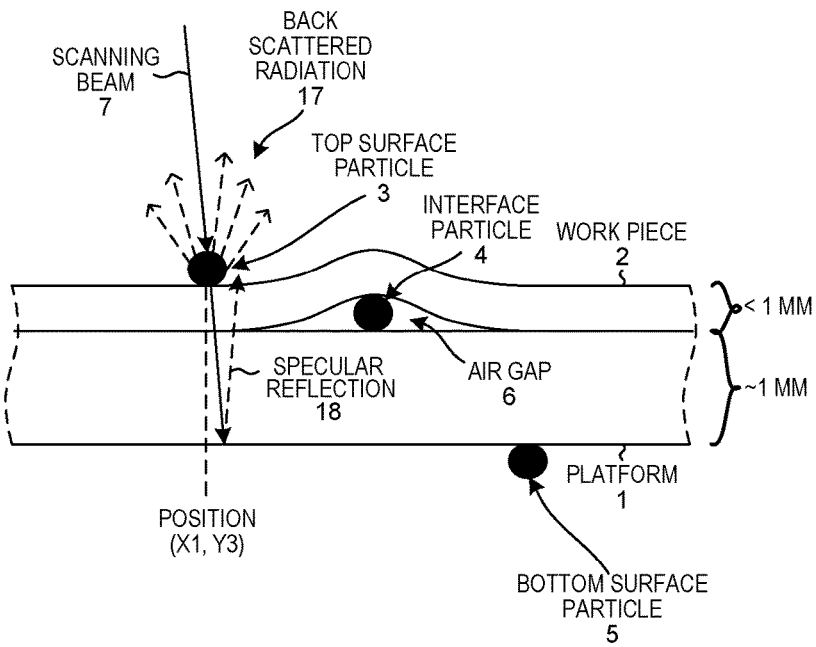
FIG. 7 is a cross-sectional diagram illustrating the interface of two transparent solids with a scanning beam directed at position located at (X1, Y3) causing top surface back scattered radiation caused by a top surface particle.

FIG. 7 is a cross-sectional diagram illustrating the interface of two transparent solids with a scanning beam 7 directed at position located at (X1, Y3) causing top surface back scattered radiation 17 caused by a top surface particle 3. Scanning beam 7 directly irradiates the top surface particle located at (X1, Y3) causing back scattered radiation 17.

Figure 8:
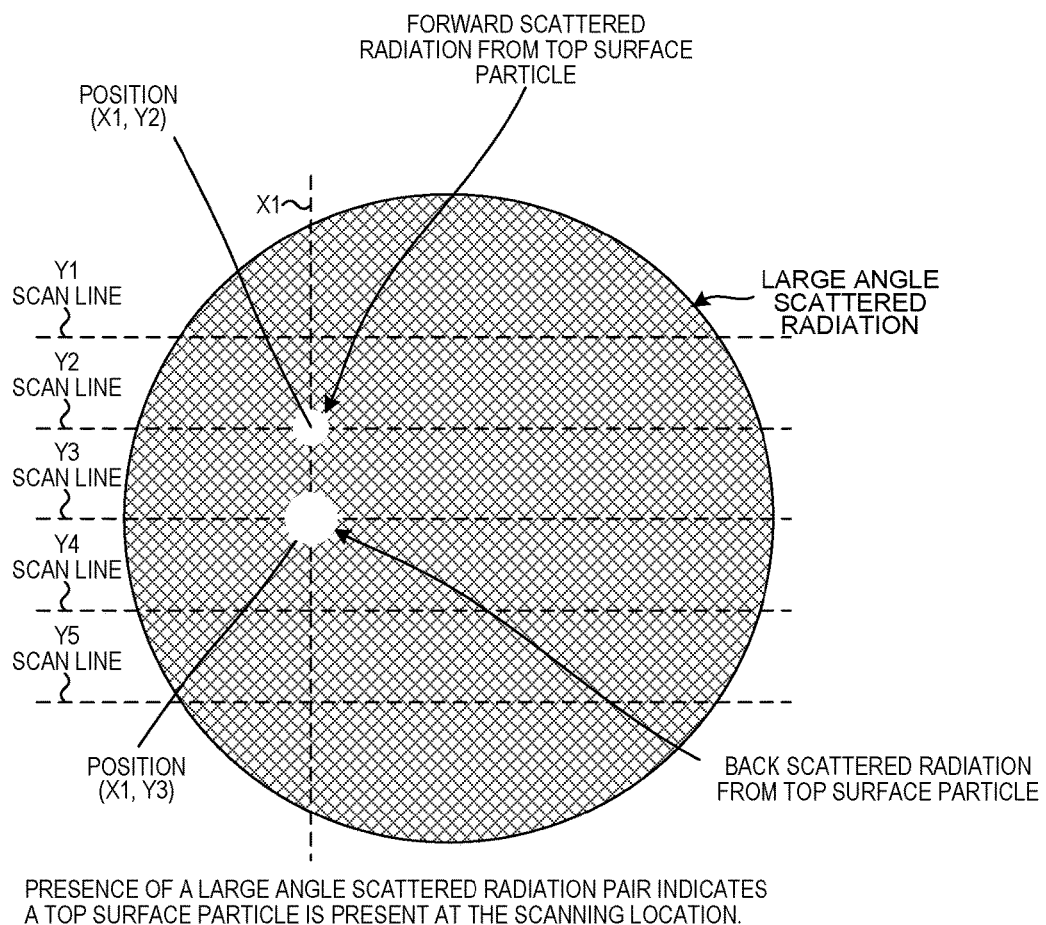
FIG. 8 is a large angle scattered radiation mapping illustrating the large angle scattered radiation resulting from the irradiation at position (X1, Y2) and position (X1, Y3) illustrated in FIGS. 6 and 7.

FIG. 8 is a large angle scattered radiation mapping illustrating the large angle scattered radiation resulting from the irradiation at position (X1, Y2) and position (X1, Y3) illustrated in FIGS. 6 and 7. The pair of large angle scattered radiation increased intensities indicates that a top surface particle is present at location (X1, Y3). The back scattered radiation intensity is significantly greater than the intensity of the forward scattered radiation.

Figure 9:
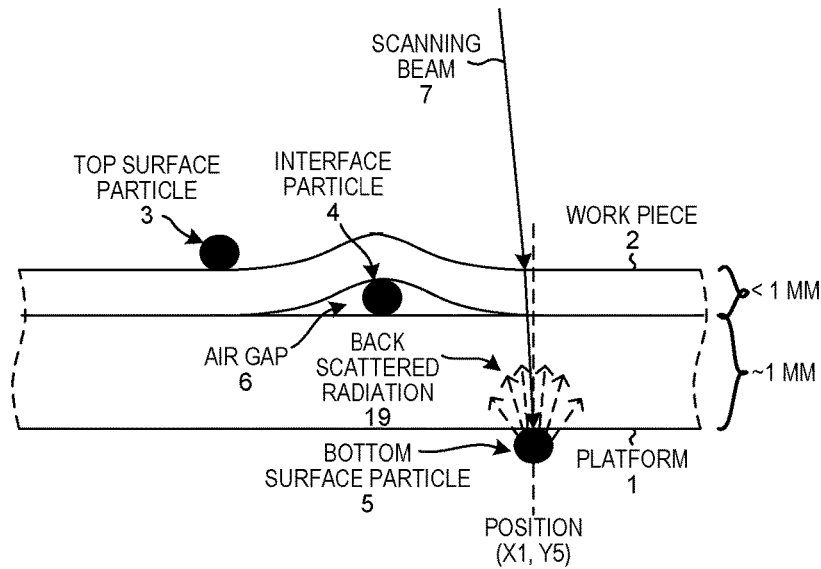
FIG. 9 is a cross-sectional diagram illustrating the interface of two transparent solids with a scanning beam directed at position located at (X1, Y5) causing bottom surface back scattered radiation caused by a bottom surface particle.

FIG. 9 is a cross-sectional diagram illustrating the interface of two transparent solids with a scanning beam directed at position located at (X1, Y5) causing bottom surface back scattered radiation caused by a bottom surface particle. Scanning beam 7 irradiates the top surface of the work piece 1 and is slightly redirected due the change in the index of refraction of air and the index of refection of the work piece 2 and causes the bottom surface particle 5 located at (X1, Y5) to be irradiated. The irradiation of the bottom surface particle 5 causes back scattered radiation 19 to emit from the bottom surface particle 5.

Figure 10:
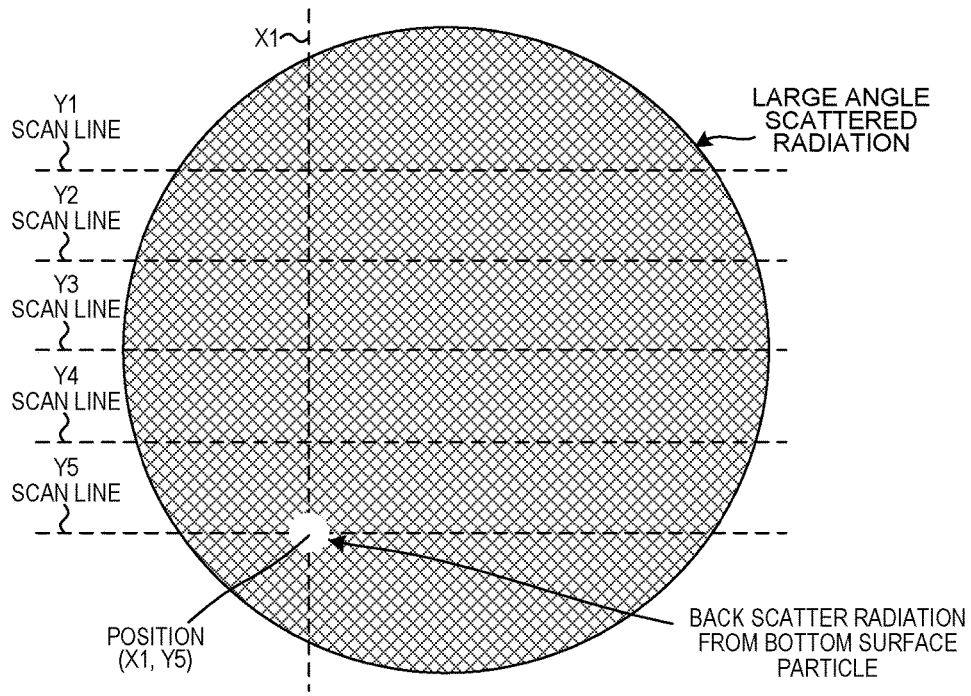
FIG. 10 is a large angle scattered radiation mapping illustrating the large angle scattered radiation resulting from the irradiation at position (X1, Y5) illustrated in FIG. 9.

FIG. 10 is a large angle scattered radiation mapping illustrating the large angle scattered radiation resulting from the irradiation of the bottom surface particle 5 located at position (X1, Y5) illustrated in FIG. 9. In contrast to two increased intensities in scattered radiation, presence of a single increased intensity in scattered radiation indicates the presence of a bottom surface particle at location (X1, Y5). In one example, two increases in scattered radiation must be within one hundred microns of each other in order to be considered a pair of increased scattered radiation intensities (also referred to herein as a "double event") and if the two increases in scattered radiation are not within one hundred microns of each other then each increase in scattered radiation is considered a single increase in scattered radiation (also referred to herein as a "single event"). In a second example, to be considered a "double event" both increases in scattered radiation must be within fifty microns of each other. As one skilled in the art will quickly ascertain, the separation limits between increased intensities of scattered radiation will vary depending on setup, environment, work piece material and thickness, platform material and thickness, and particles types to be detected.

Figure 11:
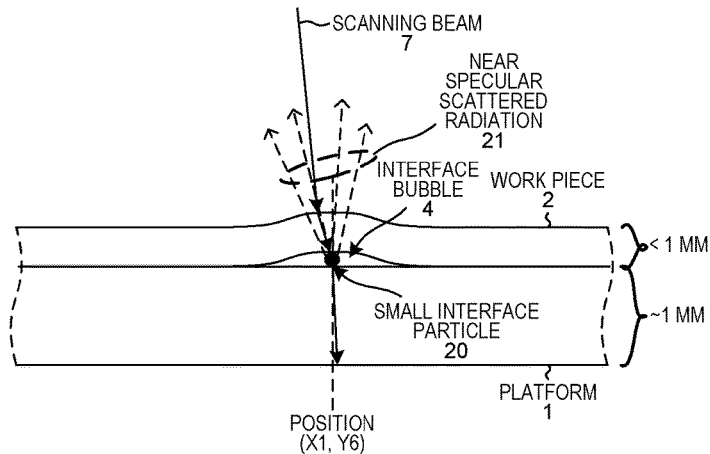
FIG. 11 is a cross-sectional diagram illustrating the interface of two transparent solids with a scanning beam directed at position located at (X1, Y6) causing near specular scattered radiation caused by an interface particle.

FIG. 11 is a cross-sectional diagram illustrating the interface of two transparent solids with a scanning beam directed at position located at (X1, Y6) causing irradiation of small interface particle 20. The irradiation of small interface particle 20 causes near specular scattered radiation 21 to emit from the small interface particle 20. The near specular scattered radiation 21 is predominately in the upward direction close to the specular reflection path.

Figure 12:
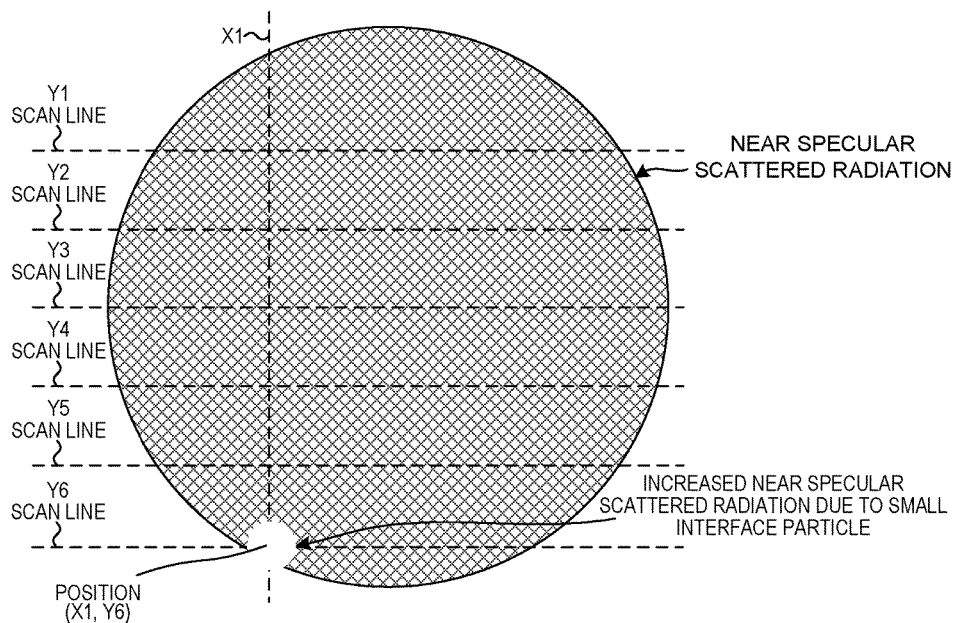
FIG. 12 is a diagram of a near specular scattered radiation mapping illustrating the near specular scattered radiation resulting from the irradiation at position (X1, Y6) illustrated in FIG. 11.

FIG. 12 is a diagram of a near specular scattered radiation mapping illustrating the near specular scattered radiation 21 resulting from the irradiation at position (X1, Y6) illustrated in FIG. 11. The increase in near specular scattered radiation (also referred to herein as "NSSR") indicates the presence of a small interface particle located at position (X1, Y6).

Figure 13:
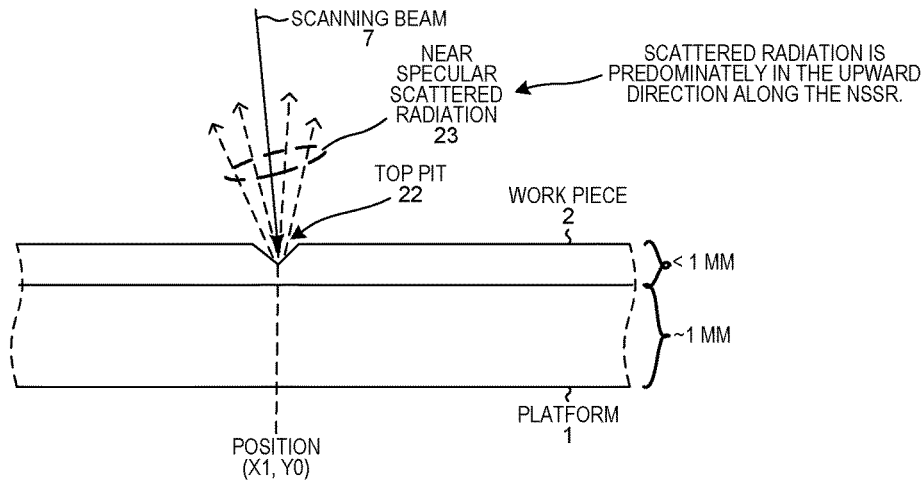
FIG. 13 is a cross-sectional diagram illustrating the interface of two transparent solids with a scanning beam directed at position located at (X1, Y0) causing near specular scattered radiation caused by a top surface pit.

FIG. 13 is a cross-sectional diagram illustrating the interface of two transparent solids with a scanning beam 7 directed at position located at (X1, Y0) causing near specular scattered radiation due to a top surface pit 22. The scattering of scanning beam 7 off the top surface pit 22 causes a near specular scattered radiation 23 to radiate from the top surface of work piece 2. The near specular scattered radiation 23 is predominately in the upward direction along the specular reflection path.

Figure 14:
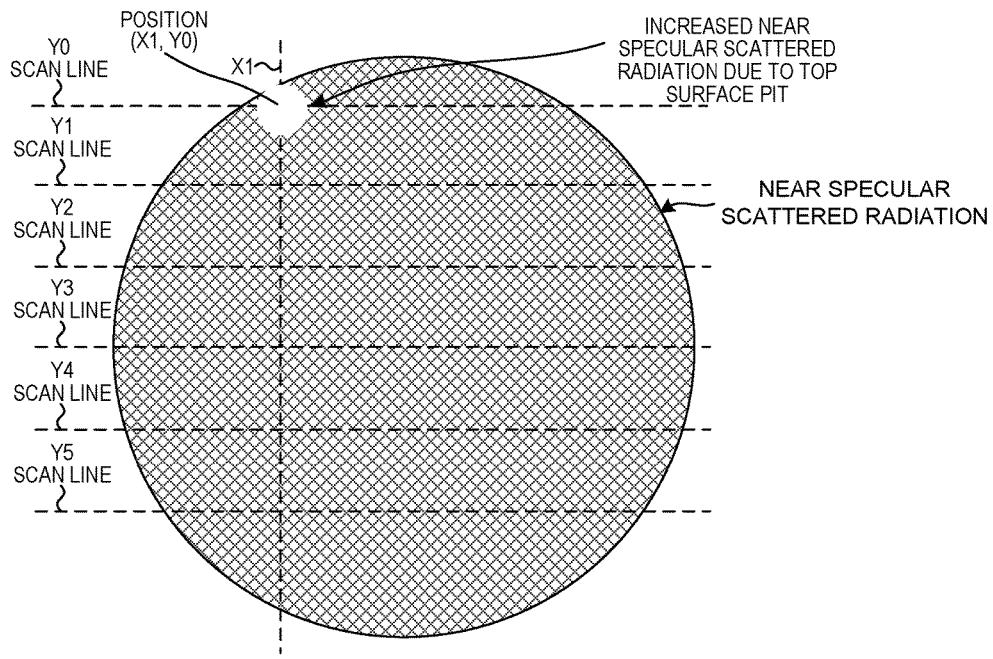
FIG. 14 is a diagram of a near specular scattered radiation mapping illustrating the near specular scattered radiation resulting from the irradiation at position (X1, Y0) illustrated in FIG. 13.

FIG. 14 is a diagram of a near specular scattered radiation mapping illustrating the near specular scattered radiation resulting from the irradiation at position (X1, Y0) illustrated in FIG. 13. An increase in near specular scattered radiation at position (X1, Y0) indicates the presence of a top surface pit at location (X1, Y0). Given that the same phenomenon is measured for a small interface particle illustrated in FIG. 12 additional measurements are required to differentiate between an increase in NSSR due to a small interface particle and an increase in NSSR due to a top surface pit. The details of these additional measurements are shown in FIG. 20.

Figure 15:
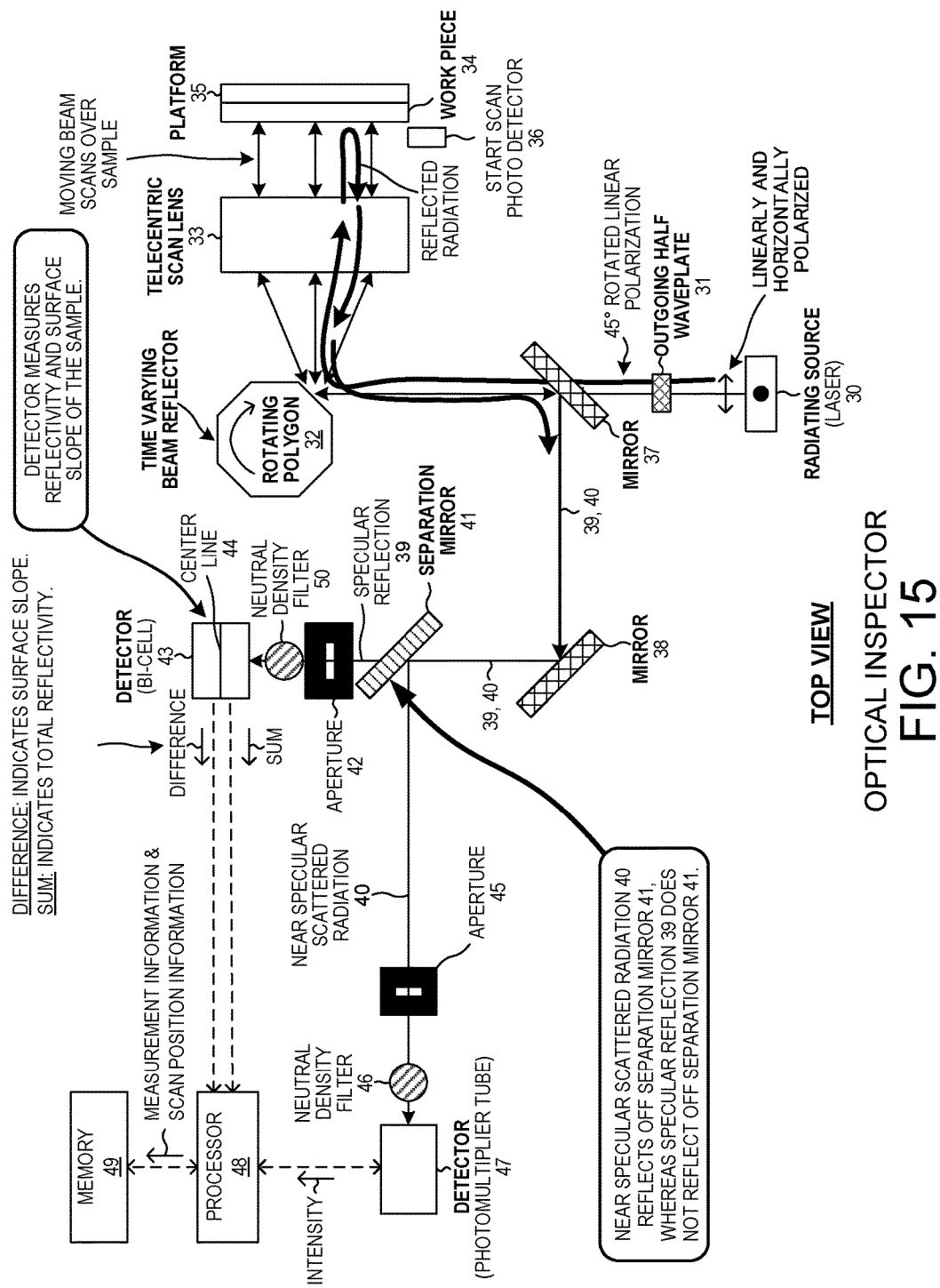
FIG. 15 is a top view diagram of a first optical inspector.

FIG. 15 is a top view diagram of an optical inspector. The optical inspector includes a radiating source 30, an outgoing half waveplate 31, a time varying beam reflector (rotating polygon 32), a telecentric scan lens 33, a start scan detector 36, a first mirror 37, a second mirror 38, a separation mirror 41, a first aperture 42, a first neutral density filter 50, a bi-cell photo detector 43, a second aperture 45, a second neutral density 46, a detector 47, a processor 48, and a memory 49. It is noted herein, the use of rotating polygon is exemplary. Any time varying beam reflector, such as a resonant galvanometer, a rotating double sided mirror, or acousto-optic beam deflector can be utilized as well.

The radiating source 30 irradiates outgoing half waveplate 31 with a source beam. In one example, the radiating source 30 is a laser. Outgoing half waveplate 31 converts the linearly polarized source beam to a forty-five degree rotated linearly polarized beam. The rotated linearly polarized beam is directed by the rotating polygon 32 to a first location on the telecentric scan lens 33. The angle at which the source beam approaches the telecentric scan lens 33 depends upon the angle of rotation of the rotating polygon 32 when the source beam contacts the rotating polygon 32. However, regardless of the angle at which the source beam approaches the telecentric scan lens 33, the telecentric scan lens 33 directs the source beam to a work piece 34 at an angle that is substantially normal to the surface of the work piece 34. In one example, the work piece is the transparent wafer (work piece 1) shown in FIG. 1 and the telecentric scan lens 33 directs the source beam to the work piece 34 at an angle of approximately three degrees from normal.

The source beam directed, at a substantially normal angle, to the work piece 34 generates a reflection of the source beam. A first portion of the reflected source beam is specular reflection. A second portion of the reflected source beam is near specular scattered radiation. Specular reflection is the mirror-like reflection of light from a surface, in which light from a single incoming direction is reflected into a single outgoing direction (in adherence with the law of reflection). Near specular scattered radiation is light which is scattered (or deflected) by defects in a region which is just outside the profile of the specular beam. Measuring both the specular reflection and the near specular scattered radiation allows the detection of defects which may not be visible in the specular reflection alone.

The reflected radiation, including specular reflection 39 and the near specular scattered radiation 40, is reflected back to the telecentric scan lens 33. The telecentric scan lens 33 directs the specular reflection 39 and the near specular scattered radiation 40 to the rotating polygon 32. The rotating polygon 32 directs the specular reflection 39 and near specular scattered radiation 40 back toward the radiating source 30. At this point, separating the source beam from the reflected light would be impractical if both the source beam and the reflected beams were traveling in the same space. To avoid this problematic situation, the radiating source 30 is placed at a location at an offset from the central axis of the telecentric scan lens 33. This directs the reflected radiation away from the radiating source 30 without altering the source beam radiating from the radiating source 30.

Mirror 37 reflects both specular reflection 39 and near specular scattered radiation 40 to mirror 38. Mirror 38 in turn reflects both specular reflection 39 and near specular scattered radiation 40 to separation mirror 41. Separation mirror 41 reflects a portion of the near specular scattered radiation 40 toward aperture 45 while not reflecting specular reflection 39. The reflected portion of the near specular scattered radiation passes through aperture 45 and neutral density filter 46 and irradiates detector 47. Specular reflection 39 passes separation mirror 41 and passes through aperture 42 and neutral density filter 50 and irradiates detector 43.

Figure 24:
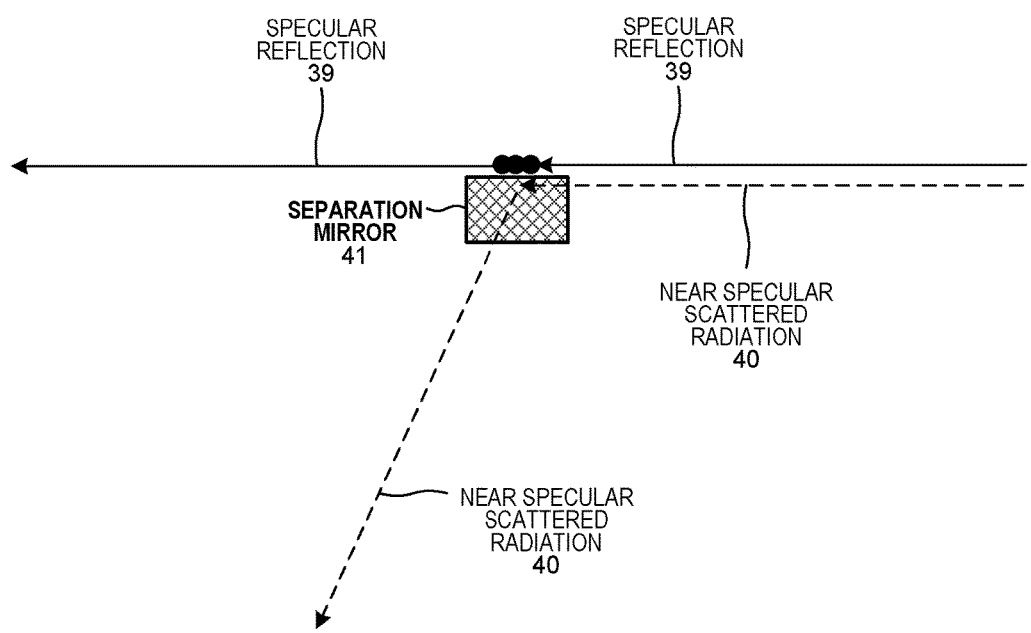
FIG. 24 is a diagram illustrating the position and functionality of a separation mirror.

Separation mirror 41 is positioned so that specular reflection 39 does not irradiate the separation mirror 41 while the near specular scattered radiation 40 does irradiate the separation mirror 41. Consequently, only a portion of the near specular scattered radiation 40 is reflected by the separation mirror 41. In a first example, the separation mirror 41 is positioned above the path of specular reflection 39. In a second example, the separation mirror 41 is positioned below the path of specular reflection 39. This example is illustrated in FIG. 24 showing the function of separation mirror 41 in greater detail.

Aperture 42 is positioned between separation mirror 41 and bi-cell detector 43. Aperture 42 serves to block any near specular scattered radiation directed toward bi-cell detector 43 from mirror 38. In an alternative example, aperture 45 is included between mirror 41 and photomultiplier tube detector 47. Aperture 45 serves to block any non-near specular scattered radiation directed toward photomultiplier tube detector 47 from separation mirror 41.

Neutral density filter 50 is positioned between aperture 42 and bi-cell detector 43. Neutral density filter 50 reduces the intensity of the specular reflection 39 that irradiates the bi-cell detector 43. The ability to vary the intensity of the specular reflection 39 provides control regarding detector sensitivity.

Neutral density filter 46 is positioned between aperture 45 and photomultiplier tube detector 47. Neutral density filter 46 reduces the intensity of the near specular scattered radiation 40 that irradiates the photomultiplier tube detector 47. The ability to vary the intensity of the near specular scattered radiation 40 provides control regarding detector sensitivity.

The bi-cell detector 43 is located such that the specular reflection 39 should irradiate the bi-cell detector 43 on the center line 44 between the two photodiodes included in the bi-cell detector 43. In the event that the surface slope (the "micro-waviness") of the work piece is not normal to the source beam, the resulting specular reflection 39 will deviate from the center line 44. A deviation from the center line 44 will cause a greater amount of the specular reflection 39 to irradiate one of the two photodiodes in the bi-cell detector 43. In response, the bi-cell detector 43 will output an increased difference value indicating a change in the slope of the work piece 34 surface. A negative difference value indicates a slope varying in a first direction. A positive difference value indicates a slope varying in a second direction. The slope measured is the surface slope of the work piece 2 in direction perpendicular to the optical scan line. Regardless of the deviation of the specular reflection 39 from the center line 44, the bi-cell detector 43 will output a sum value indicating the reflectivity of the work piece 34.

In another example, a processor 48 is also included in the top surface optical inspector shown in FIG. 15. The processor 48 receives the intensity output signal from the photomultiplier tube detector 47, a difference output signal from bi-cell detector 43, a sum output signal from bi-cell detector 43. In response, processor 48 determines whether defects are present at the scan location on the work piece 34.

The processor may also communicate with a motor controlling rotating polygon 32. The processor may increase or decrease the rate of rotation of the rotating polygon 32. For example, when switching from using a high-bandwidth detector to a low-bandwidth detector, it may be required that the rate of rotation of the rotating polygon 32 be decreased. Alternatively, when switching from using a low-bandwidth detector to a high-bandwidth detector, it may be necessary to increase the rate of rotation of the rotating polygon 32.

In another example, memory 49 is included in the top surface optical inspector shown in FIG. 15. Memory 49 stores information output by processor 48. (i.e. defect information, or defect indicator information). Memory 49 also stores location information indicating the location on the work piece which was scanned to measure the defect information or defect indicator information. Defect information is a status as to whether the scanned location on the work piece contains a defect or not. Defect indicator information includes various measurements from the scanned location on the work piece (i.e. surface slope, total reflectivity, intensity of scattered radiation, intensity of near specular scattered radiation).

The amount of near specular scattered light which is collected is limited by the size of the polygon mirror facets. The near specular scattered radiation reflects off the separation mirror 41 and is incident on the photomultiplier tube (PMT) detector. The PMT measures the intensity of the near specular scattered light. Localized defects will appear as variations (increases or decreases) in the near specular scattered light signal.

In one example, the scan of the work piece is done with the polygon rotating at a high speed and the data sampling of the bi-cell detector is run at approximately 16 MHz with the radiating source running at full intensity. Since the rotating polygon can rotate at high speeds, an entire 100 mm diameter work piece can be measured in about ten seconds.

In another example, the rotating polygon begins to spin upon power up of the device and continues to spin until the entire device is powered off. The constant spinning of the rotating polygon during operation is beneficial in that spin-up and spin-down delay time is eliminated during regular operation. The work piece is moved in the direction shown by a precision stage (not shown) to make a map of the entire work piece surface. In one embodiment, shown in FIG. 15, the optical inspector includes a start of scan photodetector 36 which is placed at the edge of the scan line and serves to trigger the acquisition of data sampling when the scanned beam passes over the detector 36.

This above process is repeated as the work piece 2 is moved underneath the optical inspector. A precision stage controller directs the movement of the work piece 34 during the inspection process. In one example, the processor 48 outputs defect inspection data which is logged along with the work piece scan location. The number and location of defects on the work piece will determine the disposition of the work piece. In one example, depending upon the location and type of defect, some portions of the work piece may be useful and others portions of the work piece may be discarded. In another example, if the work piece has many defects then the entire work piece may be discarded.

It is noted herein, that the bi-cell detector 43 is of exemplary use in this disclosure. One skilled in the art will readily realize that the bi-cell detector 38 may be replaced with various multi-cell detectors to achieve the utility of the present invention.

It is noted herein, that the use of a photomultiplier tube detector 47 is of exemplary use in this disclosure. One skilled in the art will readily realize that the photomultiplier tube detector 47 may be replaced with other light sensing detectors such as a silicon photodetector to achieve the utility of the present invention.

Figure 16:
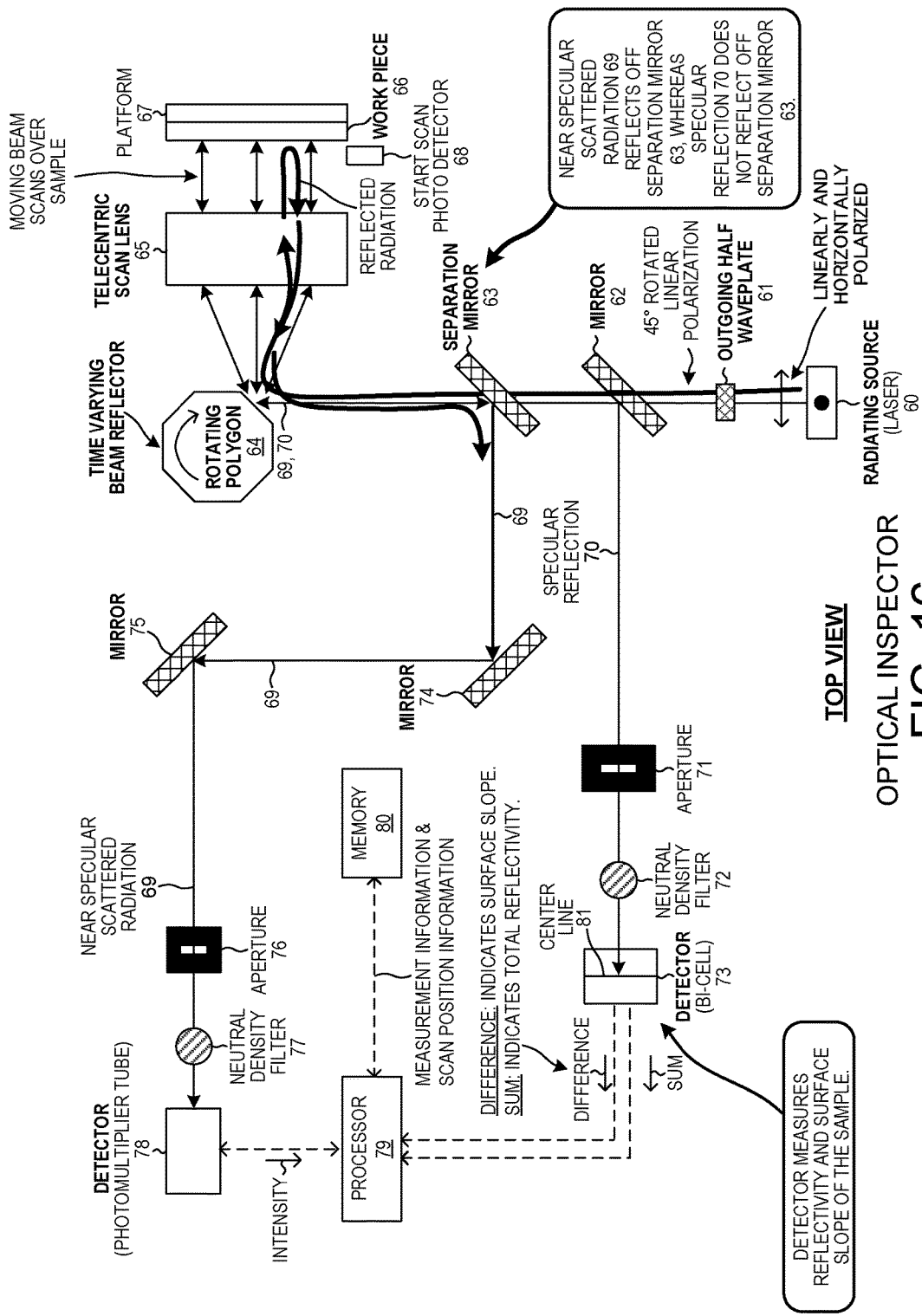
FIG. 16 is a top view diagram of a second optical inspector.

FIG. 16 is a top view diagram of a second optical inspector. The optical inspection illustrated in FIG. 16 performs the same function as the optical inspector illustrated in FIG. 15, but utilizes additional mirrors to route the specular reflection and the near specular scattered radiation along more complex paths.

Figure 17:
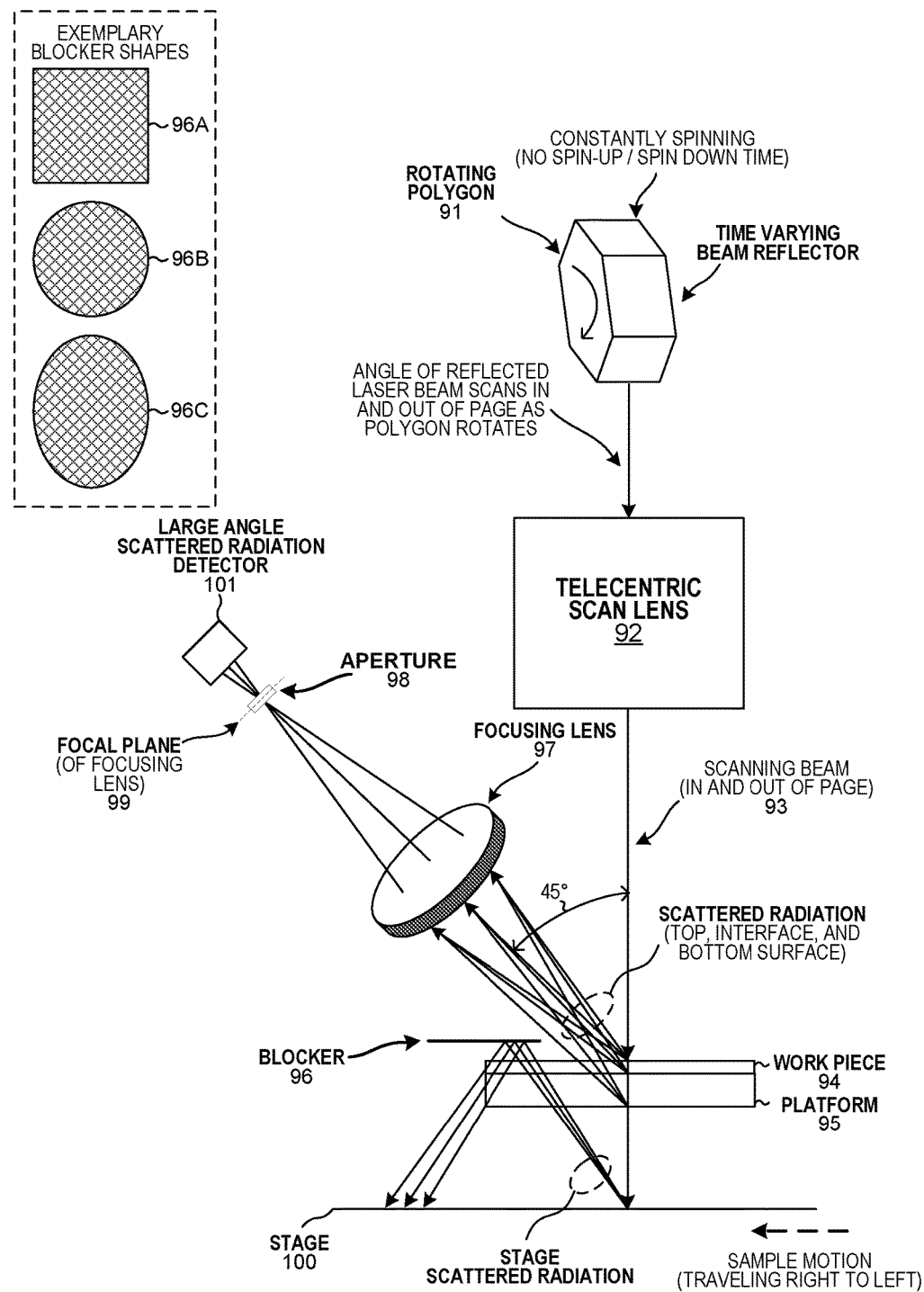
FIG. 17 is a diagram illustrating a perspective view of a large angle scattered radiation optical inspector.

FIG. 17 is a diagram illustrating a perspective view of a large angle scattered radiation optical inspector.

The optical inspector includes a rotating polygon 91 a telecentric scan lens 92, a stage 100, a blocker 96, a focusing lens 97, an aperture 98, and a detector 101. A radiation source irradiates the rotating polygon 91 which directs a moving source beam with varying angular direction onto telecentric scan lens 92. Telecentric scan lens 92 redirects the source beam with varying angular direction to an angle substantially normal to transparent work piece 94. As shown in FIG. 17, the source beam causes a scattered radiation to be radiated from transparent work piece 94 and stage 100. Scattered radiation from stage 100 occurs due to the transparency of transparent work piece 94 and transparent platform 95. A portion of scanning beam 93 passes through transparent work piece 94 and transparent platform 95 and illuminates stage 100. Stage 100 is a surface located below transparent work piece 94. Scattered radiation originating from stage 100 is illustrated in FIG. 17. Focusing lens 97, located at an oblique angle from the plane of incidence of the source beam, receives a portion of the scattered radiation originating from the transparent work piece 94 as shown in FIG. 17. The scattered radiation originating from stage 100 passes through transparent work piece 94 and travels to blocker 96 (not focusing lens 97). Blocker 96 is opaque and either absorbs or redirects scattered radiation originating from stage 100 away from focusing lens 97. As such, only scattered radiation from transparent work piece 94 or transparent platform 95 is focused by focusing lens 97 to focal plane 99. At focal plane 99, aperture 98 limits the scattered radiation allowed to pass to large angle scattered radiation detector 101. In this configuration, the scattered radiation measured by scattered radiation detector 101 includes only scattered radiation from the transparent work piece 94 and the transparent platform 95. Therefore, blocker 96 allows the measurement of scattered radiation originating from transparent work piece 94 without contamination of scattered radiation from stage 100.

In one example, blocker 96 is rectangular and opaque like the exemplary blocker labeled 96A. Blocker 96 is fixed in position with respect to the telecentric scan lens 92 and does not move during the scanning of the work piece. The scattered radiation originating from the transparent work piece 94 and transparent platform 95 is not blocked by blocker 96.

Blocker 96 may be implemented in other non-rectangular shapes, such as circularly shaped blocker 96B, or an epileptically shaped blocker 96C.

The scattered radiation originating from the transparent work piece 94 and transparent platform 95 includes scattered radiation from both the top surface and bottom surface of the transparent work piece 94 and transparent platform 95. Therefore, the scattered radiation measured by scattered radiation detector 101 includes the scattered radiation from both the top surface and bottom surfaces of both transparent work piece 94 and transparent platform 95.

Figure 18:
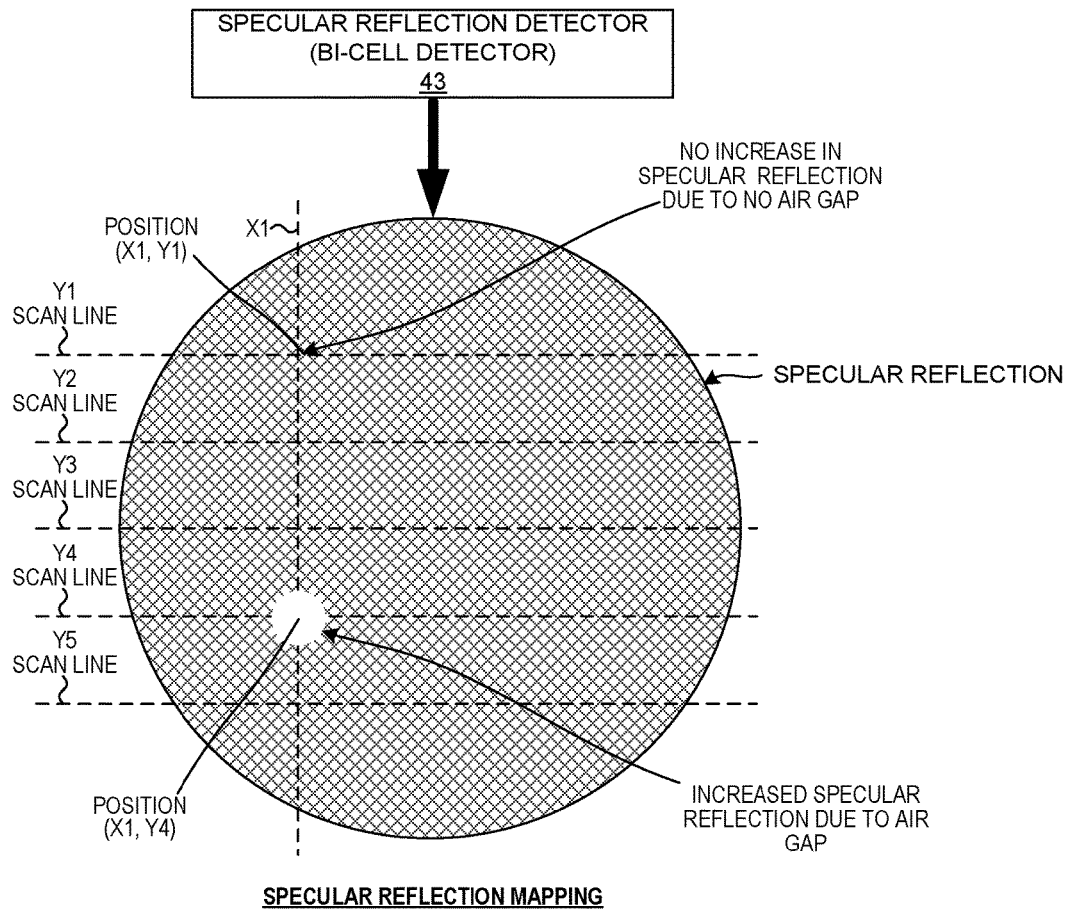
FIG. 18 is a diagram of a specular reflection intensity mapping illustrating the specular reflection resulting from the irradiation at position (X1, Y1) and (X1, Y4) illustrated in FIGS. 2 and 4.

FIG. 18 is a diagram of a specular reflection intensity mapping illustrating the specular reflection resulting from the irradiation at position (X1, Y1) and (X1, Y4) illustrated in FIGS. 2 and 4. The specular reflection intensity mapping is generated using measurements detected by bi-cell specular reflection detector 43. The measured specular reflection intensity measured at location (X1, Y1) is within the local average of specular reflection intensity which indicates that an air gap is not present at location (X1, Y1). Conversely, the measured specular reflection intensity measured at location (X1, Y4) is greater than the local average specular reflection intensity which indicates that an air gap is present at location (X1, Y4).

Figure 19:
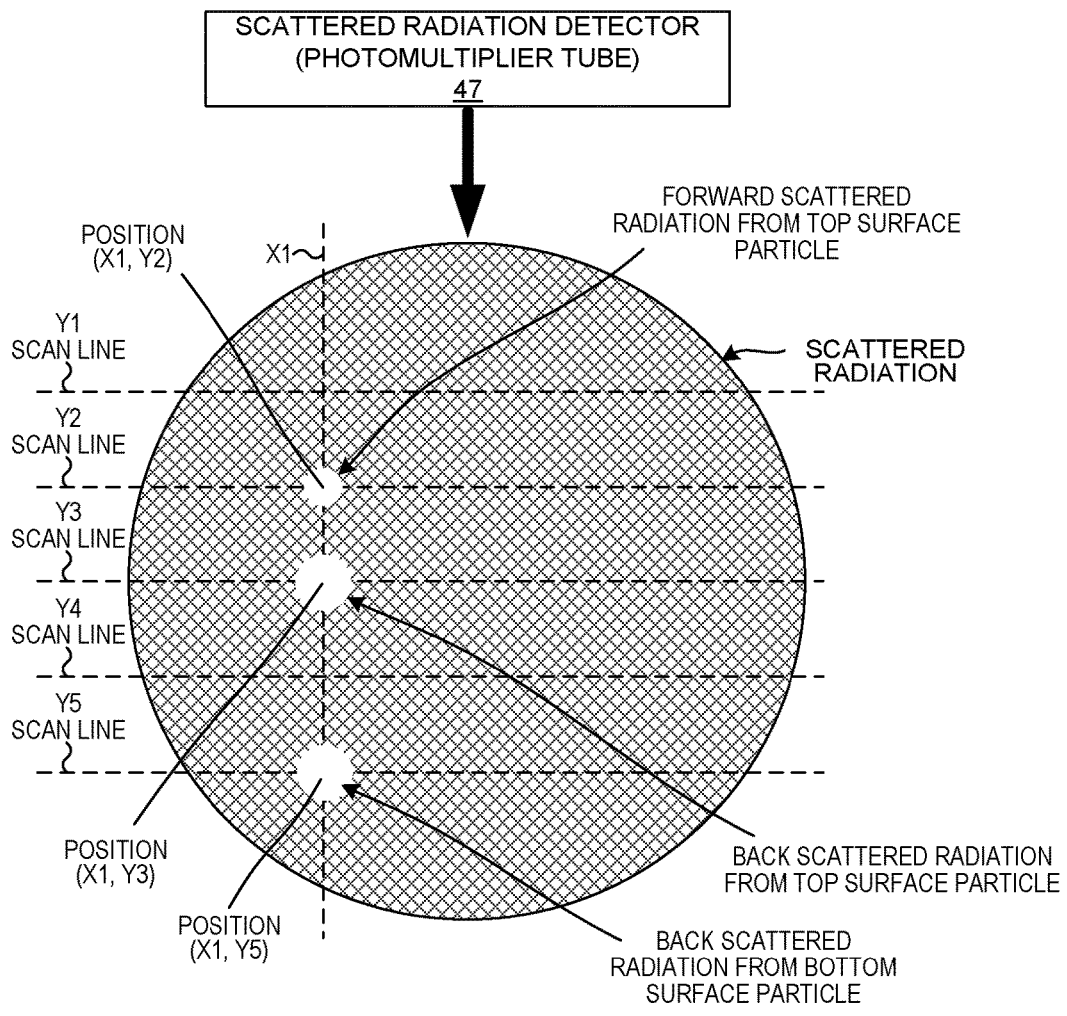
FIG. 19 is a diagram of a scattered radiation intensity mapping illustrating the scattered radiation resulting from the irradiation at position (X1, Y2), (X1, Y3), and (X1, Y5) illustrated in FIGS. 6, 7, and 9.

FIG. 19 is a diagram of a scattered radiation intensity mapping illustrating the scattered radiation resulting from the irradiation at position (X1, Y2), (X1, Y3), and (X1, Y5) illustrated in FIGS. 6, 7, and 9. The scattered radiation intensity mapping is generated using measurements detected by photomultiplier tube 47. The scattered radiation intensity measured at location (X1, Y2) is greater than the local average of scattered radiation intensity which indicates forward scattered radiation from a top surface particle. The scattered radiation intensity measured at location (X1, Y3) is much greater than the local average of scattered radiation which indicates back scattered radiation from a top surface particle. The scattered radiation intensity measured at location (X1, Y5) is much greater than the local average of scattered radiation which indicates back scattered radiation from a bottom surface particle.

Figure 21:
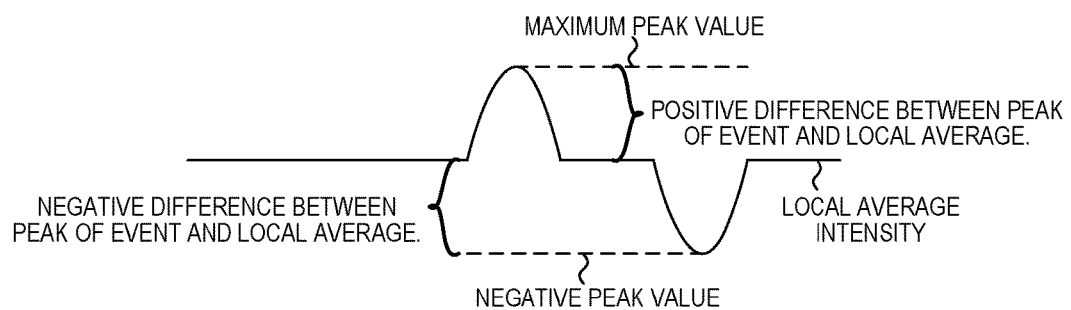
FIG. 21 is a diagram illustrating definitions of event intensities.

FIG. 20 is a diagram of defect detection and classification logic table. The table includes five columns. One column lists Large Angle Scattered Radiation (LASR) measurements. The LASR measurement is the difference between event peak and a local average of large angle scattered radiation. One column lists Near Specular Scattered Radiation (NSSR) measurements. The NSSR measurement is the difference between event peak and a local average of NSSR. An example of an event peak and a local average is illustrated in FIG. 21. One column is Specular Reflection (SR) intensity measurement. The SR is the difference between event peak and a local average of SR. One column is specular reflection angle (also referred to herein as "surface slope"). Specular reflection angle is the difference between even peak and a local average of specular reflection angle. The last column is defect type. Six types of defects are listed in the defect type column.

The first row of the table describes the characteristics of an interface particle defect. When an interface particle is present, the LASR is below a measurable threshold or is much less than NSSR measured at the same location. In one example, measured LASR intensity will be one half of the NSSR intensity measured at the same location. Conversely, the NSSR will be much great than the LASR intensity measured when an interface particle is present. The specular reflection will be constant (e.g. no significant change in intensity) or will increase when an interface particle is present. The specular reflection angle will (i) transition from a positive slope to a negative slope, or (ii) will remain at a constant slope, when an interface particle is present. When the four measurement characteristics listed above are met, the defect type is determined to be an interface particle as shown in FIG. 1.

The second row of the table describes the characteristics of an interface bubble. When an interface bubble is present, the LASR is below a measurable threshold or is much less than NSSR measured at the same location. In one example, measured LASR intensity will be one half of the NSSR intensity measured at the same location. Conversely, the NSSR will be much great than the LASR intensity measured when an interface bubble is present. The specular reflection intensity will be positive and have a large amplitude when an interface bubble is present. The specular reflection angle will oscillate between positive slope and negative slope across the interface bubble. When the four measurement characteristics listed above are met, the defect type is determined to be an interface bubble as shown in FIG. 1.

The third row of the table describes characteristics of a top surface particle. When a top surface particle is present, the LASR is much greater than the NSSR measured at the same location and the LASR shows a double event where there is another increase in LASR intensity within a close proximity to the current scan location. In one example, close proximity is within one hundred micrometers. Conversely, the NSSR will be much less than the LASR intensity measured when a top surface particle is present. The specular reflection intensity will be close to a local average of specular reflection intensity or will be less than the local average of specular reflection intensity. The specular reflection angle will not have any significant change and will remain at a constant angle (e.g. a constant slope). When the four measurement characteristics listed above are met, the defect type is determined to be a top surface particle as shown in FIG. 1.

The fourth row of the table describes characteristics of a bottom surface particle. When a bottom surface particle is present, the LASR is greater than NSSR measured at the same location and the LASR shows a single event where there is not another increase in LASR intensity within a close proximity to the current scan location. In one example, close proximity is within one hundred micrometers. Conversely, the NSSR will be much less than the LASR intensity measured when a bottom surface particle is present. The specular reflection intensity will be close to a local average of specular reflection intensities when a bottom surface particle is present. The specular reflection angle will not have any significant change and will remain at a constant angle (e.g. a constant slope). When the four measurement characteristics listed above are met, the defect type is determined to be a bottom surface particle as shown in FIG. 1.

The fifth row of the table describes characteristics of a top surface pit. When a top surface pit is present, the LASR is below a measurable threshold or is less than NSSR intensity measured at the same location. Conversely, the NSSR will be greater than the LASR intensity measured when a top surface pit is present. The specular reflection intensity decreases when a top surface pit is present. The specular reflection angle either (i) transition from a negative slope to a positive slope, or (ii) remains at a constant angle (e.g. a constant slope) when a top surface pit is present. When the four measurement characteristics listed above are met, the defect type is determined to be a top surface pit as shown in FIG. 13.

The sixth row of the table describes the characteristics of a stain. When a stain is present, the LASR is positive and the NSSR intensity measured at the same location is less than the LASR intensity. The specular reflection intensity decreases when a stain is present. The specular reflection angle does not change (e.g. constant slope) when a stain is present. When the four measurement characteristics listed above are met, the defect type is determined to be a stain.

The algorithm of FIG. 20 may be implemented by software code executed on a processor. Alternatively, the algorithm of FIG. 20 may be implemented by a state machine, lookup table or any other methodologies well known in the art.

Figure 22:
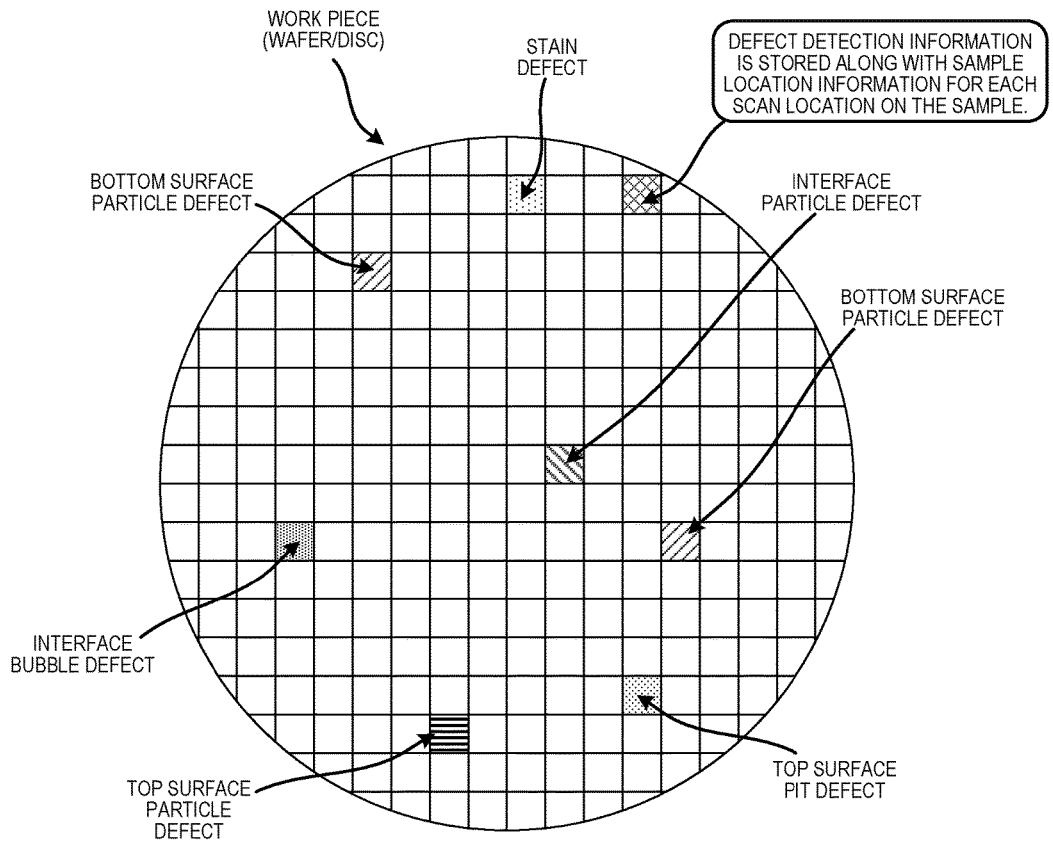
FIG. 22 illustrates a result work piece defect mapping that is generated by applying the logic described in the table of FIG. 20 to measurements measured across the surface of the work piece.

FIG. 22 illustrates a result work piece defect mapping that is generated by applying the logic described in the table of FIG. 20 to measurements measured across the surface of the work piece. The work piece defect mapping can be used by work piece manufacturers to identify the parts of the work piece that are not to have additional processing so as to not waste resources and further develop a portion of the work piece that is defective.

Figure 23:
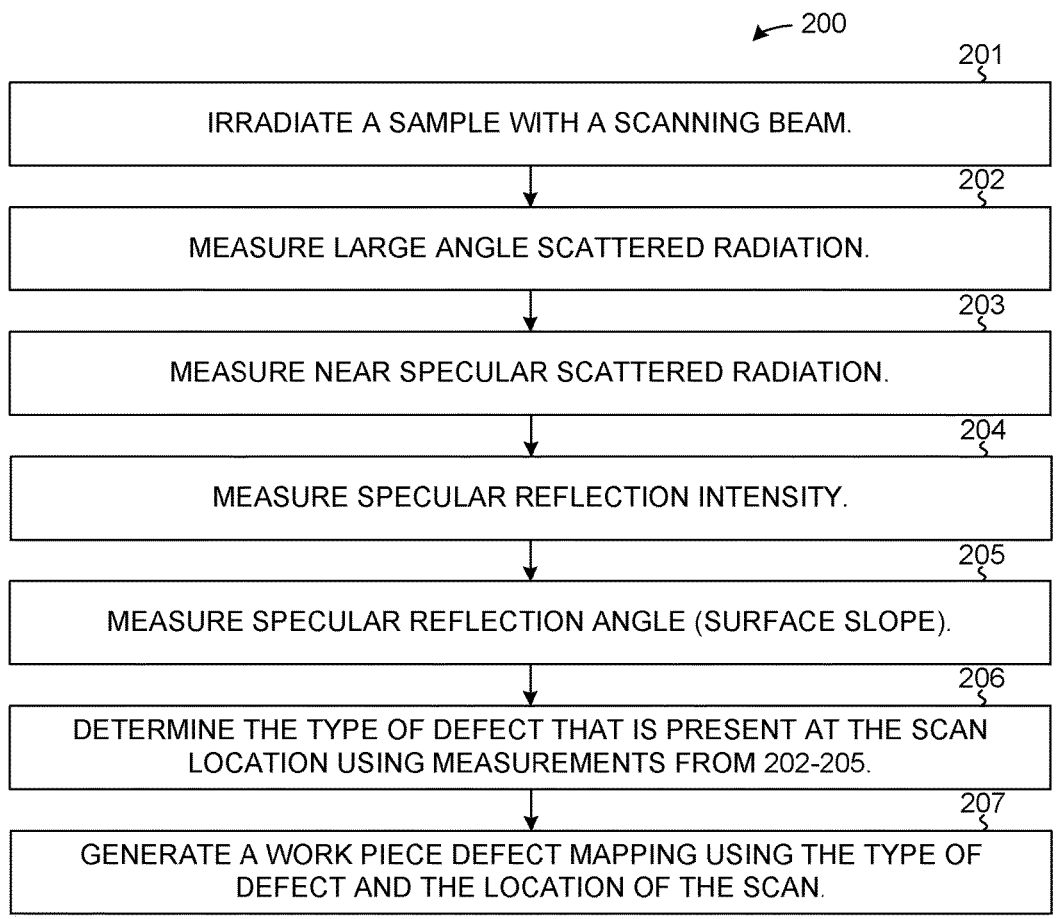
FIG. 23 is a flowchart 200 illustrating the steps included in the defect detection process.

FIG. 23 is a flowchart 200 illustrating the steps included in the defect detection process. In step 201 the work piece is irradiated with a scanning beam. In step 202 large angle scattered radiation is measured. In step 203 near specular scattered radiation is measured. In step 204 specular reflection intensity is measured. In step 205 specular reflection angle (surface slope) is measured. In one example, steps 202 through 205 are performed contemporaneously. In step 206 the type of defect that is present at the scan location is determined using the measurements taken in steps 202 through 205. In step 206 the type of defect determined in step 206 and the scanning location on the work piece is used to generate a work piece defect mapping.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method, comprising:
   (a) directing a scanning beam to a first location on a first surface of a first transparent solid, wherein a second surface of the first transparent solid abuts a first surface of a second transparent solid;
   (b) at the first location, measuring: (i) specular reflection intensity, (ii) Near Specular Scattered Radiation (NSSR) intensity, (iii) Large Angle Scattered Radiation (LASR) intensity, and (iv) Specular Reflection Angle, wherein (i) through (iv) result from irradiation by the scanning beam;
   (c) storing coordinate values of the first location, and measurements (i) through (iv) in a memory; and
   (d) determining if a type of defect is present at the first location by: (i) comparing the LASR to the NSSR, (ii) comparing the specular reflection intensity to an average specular reflection intensity, and (iii) comparing the measured specular reflection angle to a stored specular reflection angle.

2. The method of claim 1, further comprising:
   (e) repeating steps (a) through (c) at a plurality of locations on the first surface of the first transparent solid;
   (f) determining if a defect is present at each location; and
   (g) determining a type of defect when a defect is present, wherein the type of defect is selected from the group consisting of: (1) a top surface particle, (2) an interface particle, (3) a bottom surface particle, (4) an interface bubble, (5) a top surface pit, and (6) a stain.

3. The method of claim 2, wherein the type of defect at the first location is an interface particle when:
   (i) the LASR measured at the first location is less than a first percentage of the NSSR measured at the first location;
   (ii) the specular reflection intensity measured at the first location is within a second percentage of a local average of specular reflection intensity or greater; and
   (iii) the specular reflection angle transitions from a positive angle to a negative angle at the first location, wherein the local averages are a function of a plurality of measurements measured at a plurality of locations that are within a first distance of the first location.

4. The method of claim 3, wherein the first percentage is fifty percent, wherein the second percentage is a tenth of a percent, and wherein the first distance is two hundred microns.

5. The method of claim 2, wherein the type of defect at the first location is an interface bubble when:
   (i) the LASR measured at the first location is less than a first percentage of the NSSR measured at the first location;
   (ii) the specular reflection intensity measured at the first location is more than a second percentage greater than a local average of specular reflection intensity or greater; and
   (iii) the specular reflection angle oscillates between positive angles and negative angles near the first location, wherein the local averages are a function of a plurality of measurements measured at a plurality of locations that are within a first distance of the first location.

6. The method of claim 5, wherein the first percentage is fifty percent, wherein the second percentage is one half of a percent, and wherein the first distance is two hundred microns.

7. The method of claim 2, wherein the type of defect at the first location is a top surface particle when:
   (i) the LASR measured at the first location is more than a first percentage of the LASR measured at the second location, and the LASR measured at a first location is more than a second percentage of the NSSR measured at the first location, wherein the first location is within a first distance of the second location;
   (iii) the specular reflection intensity measured at the first location is within a third percentage of a local average of specular reflection intensity, or more; and
   (iv) the specular reflection angle is within a fourth percentage of a local average of specular reflection angles, wherein the local averages are a function of a plurality of measurements measured at a plurality of locations that are within a second distance of the first location.

8. The method of claim 7, wherein the first percentage is two hundred percent, wherein the second percentage is two hundred percent, wherein the third percentage is ten percent, wherein the fourth percentage is one percent, wherein the first distance is one hundred microns, and wherein the second distance is two hundred microns.

9. The method of claim 2, wherein the type of defect at the first location is bottom surface particle when:
   (i) the LASR measured at the first location is at least a first percentage of the NSSR measured at the first location;

(ii) the specular reflection intensity measured at the first location is within a second percentage of the local average of specular reflection intensity; and
(iii) the specular reflection angle is within a third percentage of a local average of specular reflection angles, wherein the local averages are a function of a plurality of measurements measured at a plurality of locations that are within a first distance of the first location.

10. The method of claim 9, wherein the first percentage is two hundred percent, wherein the second percentage is one percent, wherein the third percentage is one percent, and wherein the first distance is two hundred microns.

11. The method of claim 2, wherein the type of defect at the first location is top surface pit when:
(i) the LASR measured at the first location is within a first percentage of a local average of LASR, and less than a second percentage of the NSSR measured at the first location;
(ii) the specular reflection intensity measured at the first location is at least a third percentage less than a local average of specular reflection intensity; and
(iii) the specular reflection angle transitions from a negative angle to a positive angle at the first location, wherein the local averages are a function of a plurality of measurements measured at a plurality of locations that are within a first distance of the first location.

12. The method of claim 11, wherein the first percentage is one percent, wherein the second percentage is fifty percent, wherein the third percentage is a tenth of a percent, and wherein the first distance is two hundred microns.

13. The method of claim 2, wherein the type of defect at the first location is a stain when:
(i) the LASR measured at the first location is at least a first percentage greater than a local average of LASR intensities;
(ii) the NSSR measured at the first location is less than the LASR intensity measured at the first location;
(iii) the specular reflection intensity measured at the first location is less than a local average of specular reflection intensities; and
(iv) the specular reflection angle is within a second percentage of a local average of specular reflection angles, wherein the local averages are a function of a plurality of measurements measured at a plurality of locations that are within a first distance of the first location.

14. The method of claim 13, wherein the first percentage is a tenth of a percent, wherein the second percentage is one percent, and wherein the first distance is two hundred microns.

15. The method of claim 1, wherein steps (a) through (c) are performed without the use of an incoming waveplate, an outgoing quarter waveplate, or a polarizing beam splitter.

16. The method of claim 1, wherein the first transparent solid is one of a group consisting essential of: glass, sapphire, Silicon (Si), and Silicon Carbide (SiC).

17. The method of claim 1, wherein the second transparent solid is one of a group consisting essential of: glass, sapphire, Silicon (Si), and Silicon Carbide (SiC).

18. The method of claim 1, wherein the first and second transparent solids are transparent to infrared light.

19. The method of claim 1, wherein the first and second transparent solids are transparent to visible light.

20. The method of claim 1, wherein one of the transparent solids is transparent to visible light and the other transparent solid is transparent to infrared light.

* * * * *